United States Patent [19]

Houlihan

[11] Patent Number: 5,082,846
[45] Date of Patent: Jan. 21, 1992

[54] USE OF THE R-(+)-ISOMER OF 2-METHOXY-3-OCTADECYLOXY-PROPANOL-(1)-PHOSPHORIC ACID, MONOCHOLINE ESTER IN TREATING MULTIPLE SCLEROSIS

[75] Inventor: William J. Houlihan, Mountain Lakes, N.J.

[73] Assignee: Sandoz Ltd., Basel, Switzerland

[21] Appl. No.: 575,054

[22] Filed: Aug. 30, 1990

[51] Int. Cl.$^5$ .......................................... A61K 31/435
[52] U.S. Cl. .................................................. 514/277
[58] Field of Search ........................................ 514/277

[56] References Cited

U.S. PATENT DOCUMENTS 4,778,788 10/1988 Munder .................................. 514/77

Primary Examiner—Stanley J. Friedman
Attorney, Agent, or Firm—Gerald D. Sharkin; Robert S. Honor; Joseph J. Borovian

[57] ABSTRACT

The invention discloses the use of the R-(+)-isomer of 2-methoxy-3-octadecyloxy-propanol-(1)-phosphoric acid, monocholine ester in treating multiple sclerosis and to pharmaceutical compositions containing said isomer.

11 Claims, No Drawings

USE OF THE R-(+)-ISOMER OF 2-METHOXY-3-OCTADECYLOXY-PROPANOL-(1)-PHOSPHORIC ACID, MONOCHOLINE ESTER IN TREATING MULTIPLE SCLEROSIS

The present invention relates to the use of the R-(+)-isomer of 2-methoxy-3-octadecyloxy-propanol-(1)-phosphoric acid, monocholine ester in treating multiple sclerosis and to pharmaceutical compositions containing said isomer.

BACKGROUND OF THE INVENTION

Multiple sclerosis, a crippling nerve disorder characterized by disseminated patches of demyelination in the brain and spinal cord, has occupied the attention of research organizations for many years without, unfortunately, any appreciable success. Although ACTH (adrenocorticotropic hormone) or prednisone appears to hasten recovery in acute attacks, especially when administered early in the episode, there is no specific therapy, even today.

DESCRIPTION OF THE PRIOR ART

DOS 2,009,342 and DOS 2,009,343 disclose the use of lysolecithin compounds as immunological adjuvants.

DOS 2,619,686 discloses the use of lysolecithin compounds in treating tumors.

U.S. Pat No. 4,778,788 discloses the use of certain lysolecithin compounds in treating multiple sclerosis.

In all of the above patents, the preferred lysolecithin compound is 2-methoxy-3-octadecyloxy-propanol-(1)-phosphoric acid, monocholine ester having the formula

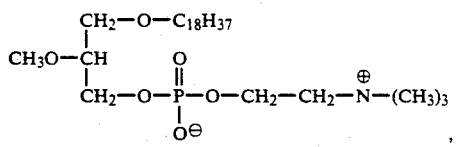

which compound is in racemic form and is more commonly referred to in the art and hereinafter as ET-18-OCH$_3$. As can be seen from the above depicted formula, ET-18-OCH$_3$ contains an asymmetric cabon atom and, therefore, is comprised of a mixture of two different isomers. Although the two different isomers have previously been isolated, e.g., in Helvetica Chimica Acta, Vol. 65, No. 100, pgs. 1059 et seq. (1982), and in spite of the fact that it is known that for a number of pharmaceutically active compounds having an asymmetric carbon atom that one isomeric form is more effective than the other, no one heretofore has investigated the pharmacological properties of the two isomeric forms of ET-18-OCH$_3$ in multiple sclerosis.

OBJECTS OF THE INVENTION

It is an object of the instant invention to provide new pharmaceutical compositions which are useful in treating multiple sclerosis.

It is another object of the instant invention to provide new pharmaceutical compositions which are useful in treating multiple sclerosis and comprise, as the active ingredient, the R-(+)-isomer of ET-18-OCH$_3$.

It is still another object of the instant invention to provide new pharmaceutical compositions which are useful in treating multiple sclerosis and comprise, as the active ingredient, the R-(+)-isomer of ET-18-OCH$_3$, and which exhibit a therapeutic advantage over known pharmaceutical compositions.

It is yet still another object of the instant invention to provide a method of treating multiple sclerosis comprising administering a therapeutically effective amount of the R-(+)-isomer of ET-18-OCH$_3$.

DESCRIPTION OF THE INVENTION

The attainment of the above objects is made possible by the surprising and unexpected discovery that the R-(+)-isomer of ET-18-OCH$_3$ is more effective than the S-(−)-isomer in treating multiple sclerosis. In comparison to known pharmaceutical compositions comprising the racemate of ET-18-OCH$_3$, the pharmaceutical compositions of the instant invention are surprisingly more effective and, therefore, offer a therapeutic advantage over the former compositions.

As indicated above, it has been surprisingly discovered that the R-(+)-isomer of ET-18-OCH$_3$ is more effective than the S-(−)-isomer in treating multiple sclerosis. This discovery can be demonstrated employing the following test methods:

Experimentally Induced Allergic Encephalomyelitis (EAE) in the Rat

[Levine et at., AM. J. PATH. 47 (1965) 61; McFarlin et al, J. IMMUNOL. 113 (1974) 712; Borel, TRANSPLANT & CLIN. IMMUNOL. 13) (1981) 3].

Male Wistar rats are injected in the hind paws with 0.1 ml. of a mixture of bovine spinal cord and complete Freund's adjuvant. The test compound is administered at dosages of from 5 to 50 mg/kg/day p.o. 5 days a week, commencing on the day of sensitization and continuing for 3 weeks. Onset of EAE in control groups receiving no medication generally commences between 9 to 16 days after sensitization and is marked by symptoms of paralysis in the hind limbs and tail. Test animals are examined daily for symptoms of the disease and disease occurrence is scored as positive when complete involvement of both hind legs and tail is observed. The test animals are kept under observation for a total period of 25 days.

On administration of the R-(+)-isomer of ET-18-OCH$_3$ at the above-indicated dosage rates, a substantial reduction of occurrence is observed over the test period in comparison with occurrence in control groups receiving placebo.

Established Experimental Allergic Encephalomyelitis (EEAE)

Testing is carried out analogously to that described above with the exception that the administration of the test compound commences on day 8 to day 9 after sensitization (i.e., immediately prior to appearance of disease symptoms) at dosages of from 5 to 50 mg/kg/day either daily or every second day and continuing for 2 weeks. During the testing period, the animals are examined daily for symptoms of the disease and scored as in the above test method.

On administration of the R-(+)-isomer of ET-18-OCH$_3$ at the above dosage rates, a substantial reduction of appearance of EAE disease symptoms is observed over the test period in comparison with appearance in control groups receiving placebo.

The precise dosage of the R-(+)-isomer of ET-18-OCH$_3$ to be employed in treating multiple sclerosis depends upon several factors including the host, the nature and the severity of the condition being treated and the mode of administration. However, in general, satisfactory inhibition of the symptoms of multiple sclerosis is achieved when the R-(+)-isomer of ET-18-OCH$_3$ is administered orally at a daily dosage of between 0.5 and 30 mg/kg body weight, preferably between 1 and 20 mg/kg, or for most larger primates, at a total daily dosage of between 100 and 600 mg. A preferred total daily dosage for most larger primates is between 100 and 300 mg.

Usually, a small dosage is administered initially and the dosage is gradually increased until the optimal dosage for the host under treatment is determined. The upper limit of dosage is that imposed by side effects, and can be determined by trial for the host being treated, including humans.

As indicated above, a preferred total daily dosage for most larger primates, e.g., humans, is 100 to 300 mg. However, it should be understood that when a clear improvement in the symptoms of multiple sclerosis is observed upon daily administration of between 100 and 300 mg of the R-(+)-isomer of ET-18-OCH$_3$, the dosage regimen can be decreased to between 100 and 300 mg of the R-(+)-isomer of ET-18-OCH$_3$ every second day.

The R-(+)-isomer of ET-18-OCH$_3$ may be combined with one or more pharmaceutically acceptable carriers and, optionally, one or more conventional pharmaceutical adjuvants and administered orally in the form of tablets, dispersible powders, granules, capsules, elixirs, suspensions and the like. The compositions may be prepared by conventional means.

The R-(+)-isomer of ET-18-OCH$_3$ may be formulated into such pharmaceutical compositions containing an amount of said isomer that is effective in treating multiple sclerosis, such compositions in unit dosage forms and such compositions comprising a solid pharmaceutically acceptable carrier.

Tablets and capsules containing the ingredients indicated below may be prepared by conventional techniques and are useful in treating multiple sclerosis when administered once a day.

| Ingredients | Weight (mg) | |
| --- | --- | --- |
| | tablet | capsule |
| R-(+)-isomer of ET-18-OCH$_3$ | 150 | 150 |
| tragacanth | 10 | — |
| lactose (spray-dried) | 197.5 | 250 |
| corn starch | 25 | — |
| talcum | 15 | — |
| magnesium stearate | 2.5 | — |
| Total | 400.0 | 400.0 |

The preferred pharmaceutical compositions from the standpoint of preparation and ease of administration are solid compositions, particularly liquid or hard-filled capsules and tablets containing from about 100–300 milligrams of the R-(+)-isomer of ET-18-OCH$_3$.

The R-(+)-isomer of ET-18-OCH$_3$ for use in the method and compositions of the instant invention can be prepared by any of a variety of methods described in the literature, e.g., by resolution of end or intermediate products or by employing optically active starting materials.

RESULTS

Employing the EAE method described above, the following results were obtained when ET-18-OCH$_3$ in racemic form and the corresponding R-(+) and S-(−) isomers were administered at 25 mg/kg over a period of 14 days.

| | No. of animals with total paralysis | Total No. of animals | % |
| --- | --- | --- | --- |
| ET-18-OCH$_3$ (in racemic form) | 9 | 19 | 47 |
| R-(+)-isomer of ET-18-OCH$_3$ | 1 | 6 | 17 |
| S-(−)-isomer of ET-18-OCH$_3$ | 7 | 7 | 100 |

As can be seen from the above results, the S-(−)-isomer of ET-18-OCH$_3$ appears to be devoid of any usefulness in treating multiple sclerosis upon administration of 25 mg/kg of said isomer in the above method. Moreover, it can be seen that the R-(+)-isomer is more effective in treating multiple sclerosis than is ET-18-OCH$_3$ in racemic form and that, therefore, it can be concluded that pharmaceutical compositions comprising the R-(+)-isomer of ET-18-OCH$_3$, as the active ingredient, offer a therapeutic advantage over known pharmaceutical compositions comprising ET-18-OCH$_3$ in racemic form.

What is claimed is:

1. A pharmaceutical composition useful in treating multiple sclerosis comprising a pharmaceutically acceptable carrier or diluent and a therapeutically effective amount of the R-(+)-isomer of 2-methoxy-3-octadecyloxy-propanol-(1)-phosphoric acid, monocholine ester.

2. A composition according to claim 1 in unit dosage form.

3. A composition according to claim 2 wherein the unit dosage form is a tablet.

4. A composition according to claim 2 wherein the unit dosage form is a capsule.

5. A composition according to claim 1 comprising from 100 to 600 mg of the R-(+)-isomer.

6. A composition according to claim 5 comprising from 100 to 300 mg of the R-(+)-isomer.

7. A method of treating multiple sclerosis comprising administering to a subject in need of such treatment a therapeutically effective amount of the R-(+)-isomer of 2-methoxy-3-octadecyloxy-propanol-(1)-phosphoric acid, monocholine ester.

8. A method according to claim 7 wherein the R-(+)-isomer is administered at a daily dosage of between 0.5 and 30 mg/kg body weight.

9. A method according to claim 8 wherein the R-(+)-isomer is administered at a daily dosage of between 1 and 20 mg/kg body weight.

10. A method according to claim 7 wherein the R-(+)-isomer is administered at a daily dosage of between 100 and 600 mg.

11. A method according to claim 10 wherein the R-(+)-isomer is administered at a daily dosage of between 100 and 300 mg.

* * * * *